(12) United States Patent
Linder et al.

(10) Patent No.: US 9,254,213 B2
(45) Date of Patent: Feb. 9, 2016

(54) STENT DELIVERY DEVICE

(75) Inventors: Richard J. Linder, Sandy, UT (US); Daryl R. Edmiston, Sandy, UT (US); Steven W. Johnson, West Jordan, UT (US); Adriana Margarita Topete, Bountiful, UT (US)

(73) Assignee: RUBICON MEDICAL, INC., Salt Lake City, UT (US)

( * ) Notice: Subject to any disclaimer, the term of this patent is extended or adjusted under 35 U.S.C. 154(b) by 2643 days.

(21) Appl. No.: 11/017,561

(22) Filed: Dec. 20, 2004

(65) Prior Publication Data

US 2005/0154443 A1    Jul. 14, 2005

Related U.S. Application Data

(60) Provisional application No. 60/535,324, filed on Jan. 9, 2004.

(51) Int. Cl.
| | |
|---|---|
| A61F 2/97 | (2013.01) |
| A61F 2/95 | (2013.01) |
| A61F 2/966 | (2013.01) |
| A61F 2/01 | (2006.01) |
| A61F 2/958 | (2013.01) |

(52) U.S. Cl.
CPC ... *A61F 2/97* (2013.01); *A61F 2/95* (2013.01); *A61F 2/966* (2013.01); *A61F 2/013* (2013.01); *A61F 2/958* (2013.01); *A61F 2002/9511* (2013.01)

(58) Field of Classification Search
CPC ........................................................ A61F 2/97
USPC ............. 623/1.11, 1.12, 1.16, 1.2, 1.23, 1.44; 606/191
See application file for complete search history.

(56) References Cited

U.S. PATENT DOCUMENTS

| | | |
|---|---|---|
| 4,878,906 A | 11/1989 | Lindemann et al. |
| 5,026,377 A | 6/1991 | Burton et al. |
| 5,078,720 A | 1/1992 | Burton et al. |
| 5,201,757 A | 4/1993 | Heyn et al. |
| 5,441,515 A | 8/1995 | Khosravl et al. |
| 5,445,646 A | 8/1995 | Euteneuer et al. |
| 5,480,423 A | 1/1996 | Ravenscroft et al. |
| 5,549,635 A | 8/1996 | Solar |
| 5,549,662 A | 8/1996 | Fordenbacher |
| 5,571,135 A | 11/1996 | Fraser et al. |
| 5,607,466 A | 3/1997 | Imbert et al. |
| 5,618,299 A | 4/1997 | Khosravi et al. |
| 5,643,278 A | 7/1997 | Wijay |
| 5,645,559 A | 7/1997 | Hachtman et al. |
| 5,662,703 A | 9/1997 | Yurek et al. |

(Continued)

*Primary Examiner* — (Jackie) Tan-Uyen T. Ho
*Assistant Examiner* — Thomas McEvoy
(74) *Attorney, Agent, or Firm* — Seager, Tufte & Wickhem LLP

(57) ABSTRACT

A stent delivery device comprises a guide member having a proximal end and a distal end, and a stent mounted to the guide member. A restraining member positioned about the stent comprises two or more portions that are held together by one or more actuating members. The one or more actuating members can be positioned by a user in a proximal direction, since the one or more actuating members extend to the proximal end, or handle, of the guide member. When a user moves the one or more actuating members in a proximal direction, the one or more actuating members slide away from the two or more portions, allowing the stent to expand. The stent delivery device can further be configured to include an embolic protection component.

8 Claims, 9 Drawing Sheets

(56) References Cited

U.S. PATENT DOCUMENTS

| | | | |
|---|---|---|---|
| 5,669,932 A | 9/1997 | Fischell et al. |
| 5,707,376 A | 1/1998 | Kavteladze et al. |
| 5,725,571 A | 3/1998 | Imbert et al. |
| 5,733,328 A | 3/1998 | Fordenbacher |
| 5,743,874 A | 4/1998 | Fischell et al. |
| 5,797,952 A | 8/1998 | Klein |
| 5,817,102 A | 10/1998 | Johnson et al. |
| 5,824,058 A | 10/1998 | Ravenscroft et al. |
| 5,876,448 A | 3/1999 | Thompson et al. |
| 5,910,154 A | 6/1999 | Tsugita et al. |
| 5,911,734 A | 6/1999 | Tsugita et al. |
| 5,968,052 A | 10/1999 | Sullivan, III et al. |
| 5,984,957 A | 11/1999 | Laptewicz, Jr. et al. |
| 5,989,280 A | 11/1999 | Euteneuer et al. |
| 6,019,778 A | 2/2000 | Wilson et al. |
| 6,019,787 A | 2/2000 | Richard et al. |
| 6,027,520 A | 2/2000 | Tsugita et al. |
| 6,036,725 A | 3/2000 | Avellanet |
| 6,042,598 A | 3/2000 | Tsugita et al. |
| 6,077,295 A | 6/2000 | Limon et al. |
| 6,090,035 A | 7/2000 | Campbell et al. |
| 6,093,203 A | 7/2000 | Uflacker |
| 6,120,522 A | 9/2000 | Vrba et al. |
| 6,132,458 A | 10/2000 | Staehle et al. |
| 6,136,006 A | 10/2000 | Johnson et al. |
| 6,146,415 A | 11/2000 | Fitz |
| 6,165,200 A | 12/2000 | Tsugita et al. |
| 6,183,481 B1 | 2/2001 | Lee et al. |
| 6,200,336 B1 | 3/2001 | Pavcnik et al. |
| 6,210,431 B1 | 4/2001 | Power |
| 6,214,036 B1 | 4/2001 | Letendre et al. |
| 6,224,627 B1 | 5/2001 | Armstrong et al. |
| 6,238,402 B1 | 5/2001 | Sullivan, III et al. |
| 6,241,758 B1 | 6/2001 | Cox |
| 6,245,100 B1 | 6/2001 | Davlla et al. |
| 6,251,132 B1 | 6/2001 | Ravenscroft et al. |
| 6,254,609 B1 | 7/2001 | Vrba et al. |
| 6,254,627 B1 | 7/2001 | Freidberg |
| 6,264,684 B1 | 7/2001 | Banas et al. |
| 6,267,783 B1 | 7/2001 | Letendre et al. |
| 6,280,465 B1 | 8/2001 | Cryer |
| 6,287,329 B1 | 9/2001 | Duerig et al. |
| 6,296,661 B1 | 10/2001 | Davila et al. |
| 6,302,893 B1 | 10/2001 | Limon et al. |
| 6,306,163 B1 | 10/2001 | Fitz |
| 6,315,708 B1 | 11/2001 | Salmon et al. |
| 6,315,792 B1 | 11/2001 | Armstrong et al. |
| 6,368,344 B1 | 4/2002 | Fitz |
| 6,368,355 B1 | 4/2002 | Uflacker |
| 6,375,676 B1 | 4/2002 | Cox |
| 6,375,791 B1 | 4/2002 | Chiesl, III et al. |
| 6,391,050 B1 | 5/2002 | Broome |
| 6,391,051 B2 | 5/2002 | Sullivan, III et al. |
| 6,425,898 B1 | 7/2002 | Wilson et al. |
| 6,447,540 B1 | 9/2002 | Fontaine et al. |
| 6,451,047 B2 | 9/2002 | McCrea et al. |
| 6,468,298 B1 | 10/2002 | Pelton |
| 6,471,718 B1 | 10/2002 | Staehle et al. |
| 6,485,510 B1 * | 11/2002 | Camrud et al. ............... 623/1.16 |
| 6,508,833 B2 | 1/2003 | Pavcnik et al. |
| 6,517,547 B1 | 2/2003 | Feeser et al. |
| 6,530,947 B1 | 3/2003 | Euteneuer et al. |
| 6,533,807 B2 | 3/2003 | Wolinsky et al. |
| 6,537,295 B2 | 3/2003 | Petersen |
| 6,540,722 B1 | 4/2003 | Boyle et al. |
| 6,551,341 B2 | 4/2003 | Boylan et al. |
| 6,569,191 B1 | 5/2003 | Hogan |
| 6,576,006 B2 | 6/2003 | Limon et al. |
| 6,602,272 B2 | 8/2003 | Boylan et al. |
| 6,613,072 B2 * | 9/2003 | Lau et al. .................... 623/1.11 |
| 6,613,075 B1 | 9/2003 | Healy et al. |
| 6,632,223 B1 | 10/2003 | Keane |
| 6,656,212 B2 | 12/2003 | Ravenscroft et al. |
| 6,656,213 B2 | 12/2003 | Solem |
| 6,666,884 B1 | 12/2003 | Webster |
| 6,669,718 B2 | 12/2003 | Besselink |
| 6,673,101 B1 | 1/2004 | Fitzgerald et al. |
| 6,676,682 B1 | 1/2004 | Tsugita et al. |
| 6,676,692 B2 | 1/2004 | Rabkin et al. |
| 6,676,693 B1 | 1/2004 | Belding et al. |
| 6,679,902 B1 | 1/2004 | Boyle et al. |
| 6,679,909 B2 | 1/2004 | McIntosh et al. |
| 6,695,813 B1 | 2/2004 | Boyle et al. |
| 6,695,862 B2 | 2/2004 | Cox et al. |
| 6,702,834 B1 | 3/2004 | Boylan et al. |
| 6,706,053 B1 | 3/2004 | Boylan et al. |
| 6,709,454 B1 | 3/2004 | Cox et al. |
| 6,726,712 B1 | 4/2004 | Raeder-Devens et al. |
| 6,743,219 B1 | 6/2004 | Dwyer et al. |
| 6,758,858 B2 | 7/2004 | McCrea et al. |
| 6,773,446 B1 | 8/2004 | Dwyer et al. |
| 6,786,918 B1 | 9/2004 | Krivoruchko et al. |
| 6,790,221 B2 | 9/2004 | Monroe et al. |
| 6,797,217 B2 | 9/2004 | McCrea et al. |
| 6,827,731 B2 | 12/2004 | Armstrong et al. |
| 6,837,901 B2 | 1/2005 | Rabkin et al. |
| 6,840,950 B2 | 1/2005 | Stanford et al. |
| 6,843,802 B1 | 1/2005 | Villalobos et al. |
| 6,859,986 B2 | 3/2005 | Jackson et al. |
| 6,860,898 B2 | 3/2005 | Stack et al. |
| 6,890,337 B2 | 5/2005 | Feeser et al. |
| 6,893,458 B2 | 5/2005 | Cox et al. |
| 6,899,727 B2 | 5/2005 | Armstrong et al. |
| 6,902,575 B2 | 6/2005 | Laakso et al. |
| 6,926,732 B2 | 8/2005 | Derus et al. |
| 6,939,368 B2 | 9/2005 | Simso |
| 6,964,673 B2 | 11/2005 | Tsugita et al. |
| 2002/0004676 A1 * | 1/2002 | Wallace et al. ............. 623/1.12 |
| 2002/0099436 A1 | 7/2002 | Thornton et al. |
| 2003/0149467 A1 * | 8/2003 | Linder et al. ............... 623/1.11 |

\* cited by examiner

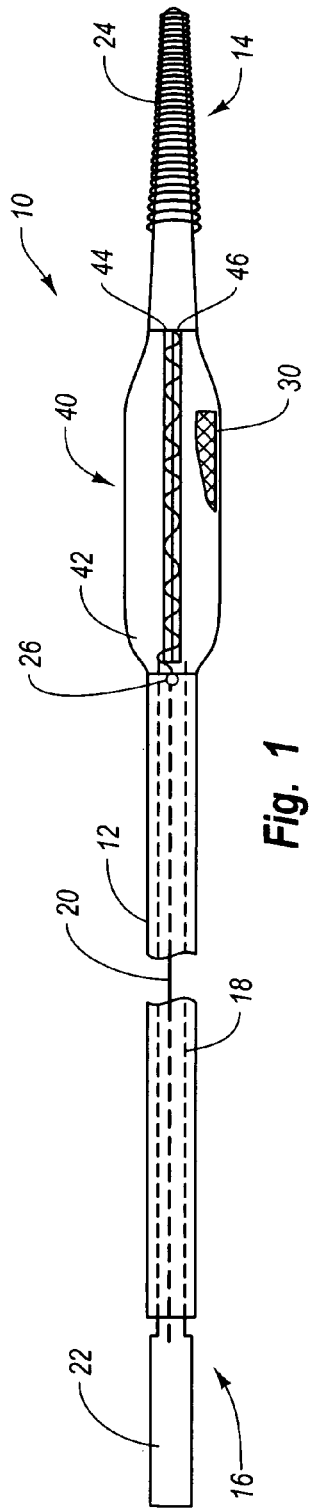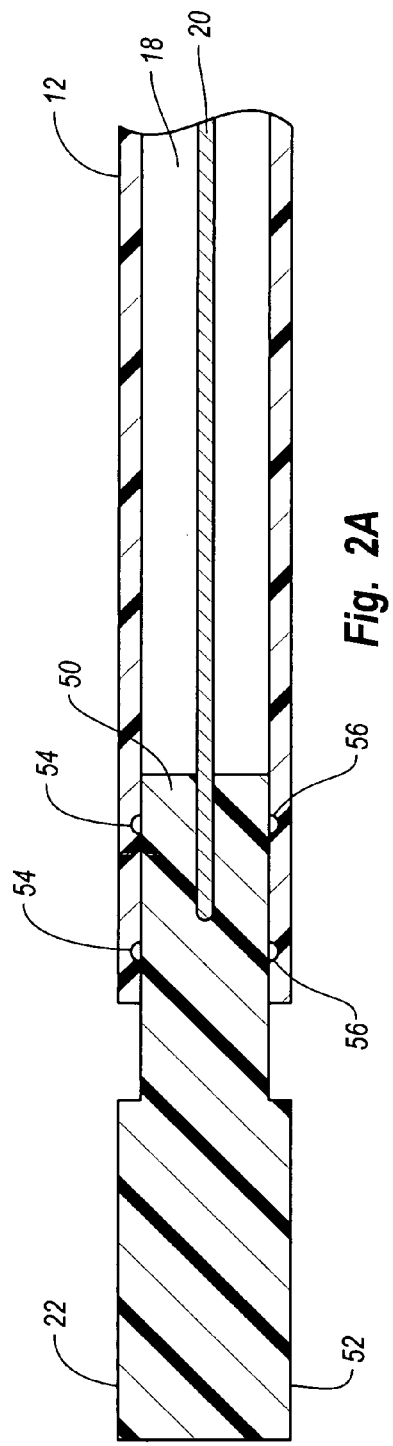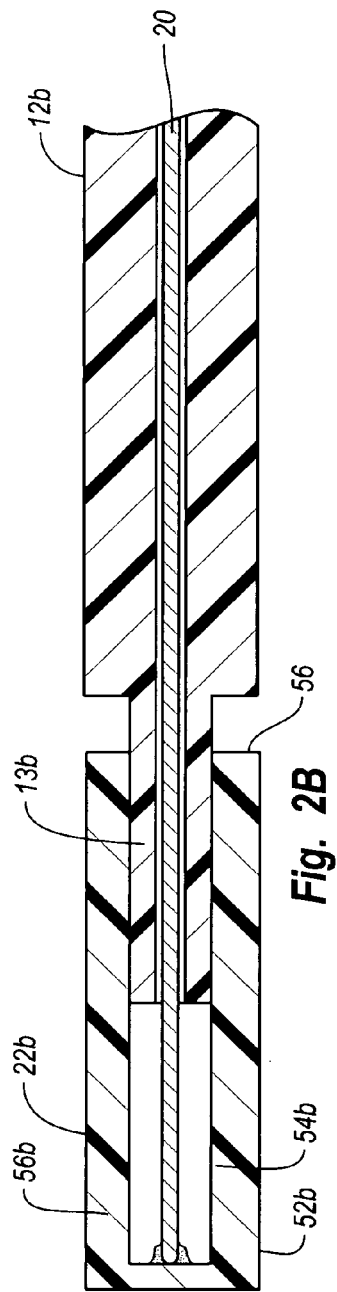

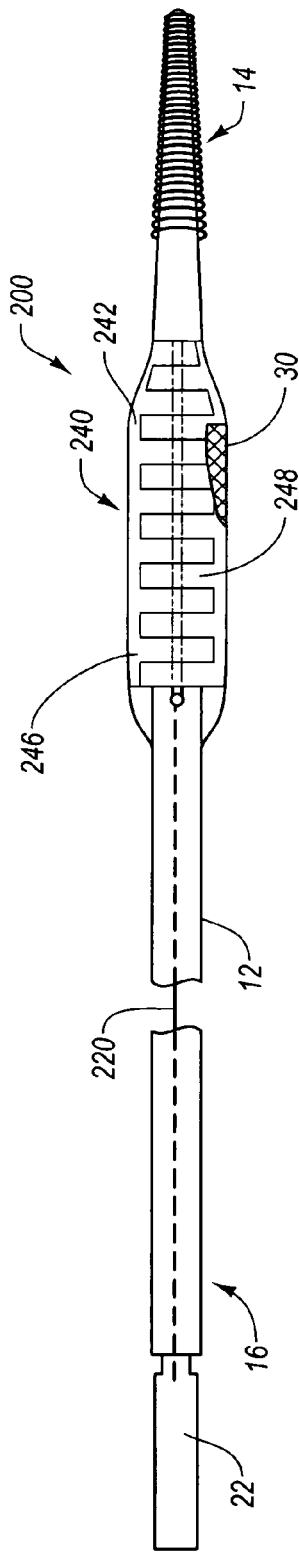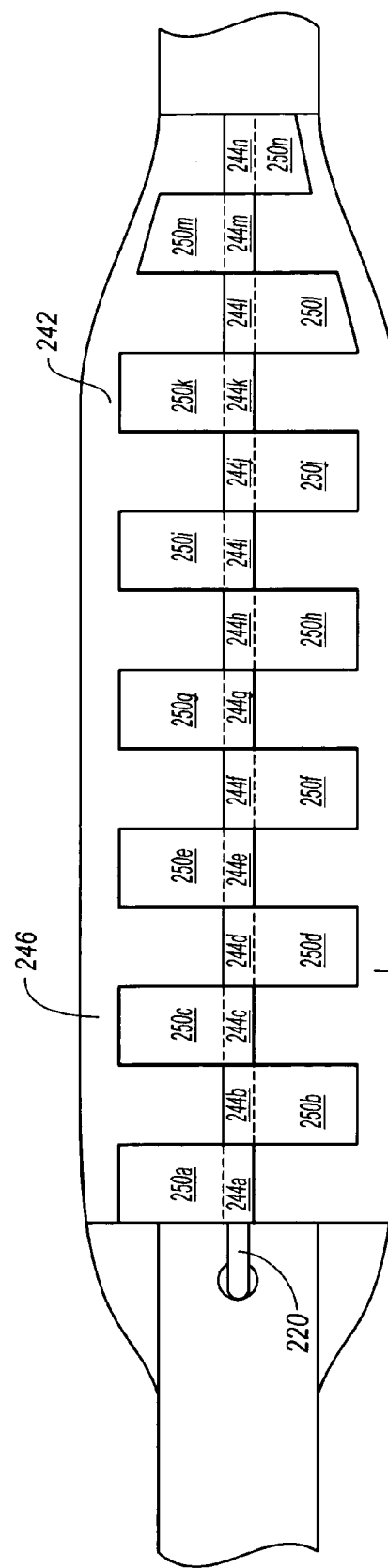
Fig. 6
Fig. 7

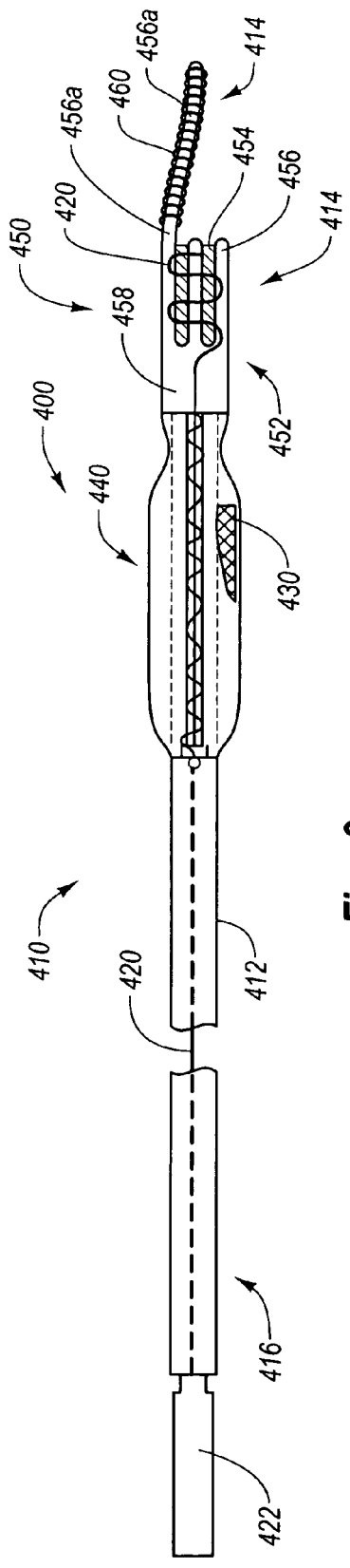
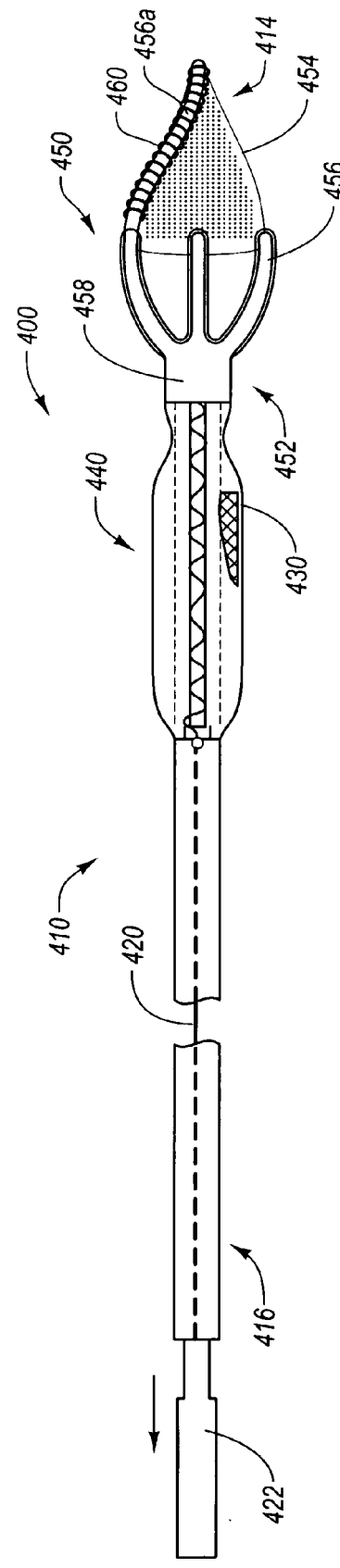
Fig. 9
Fig. 10

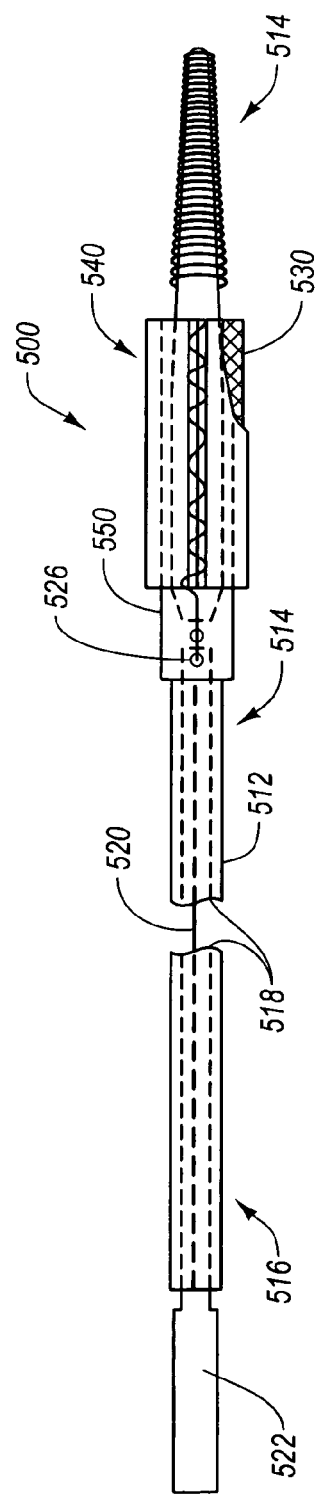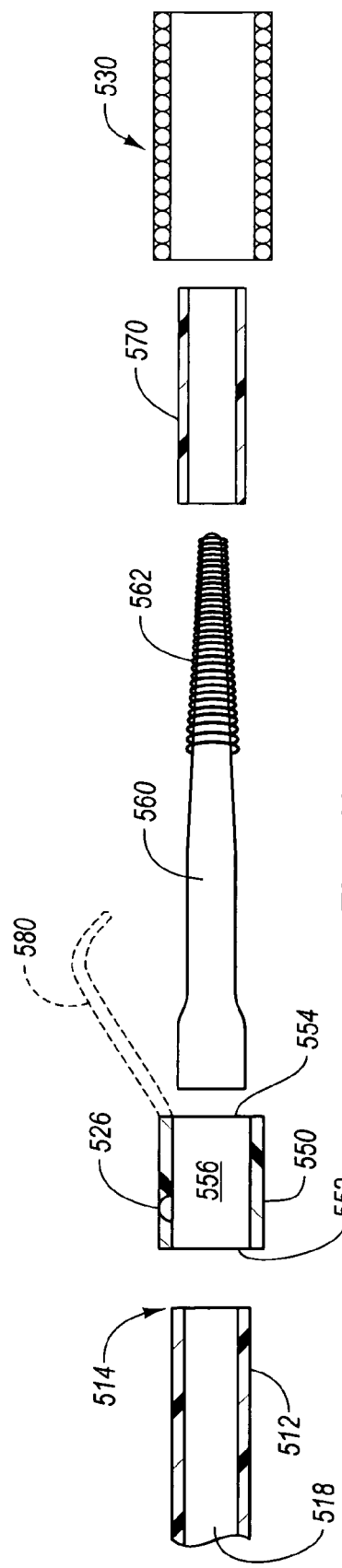

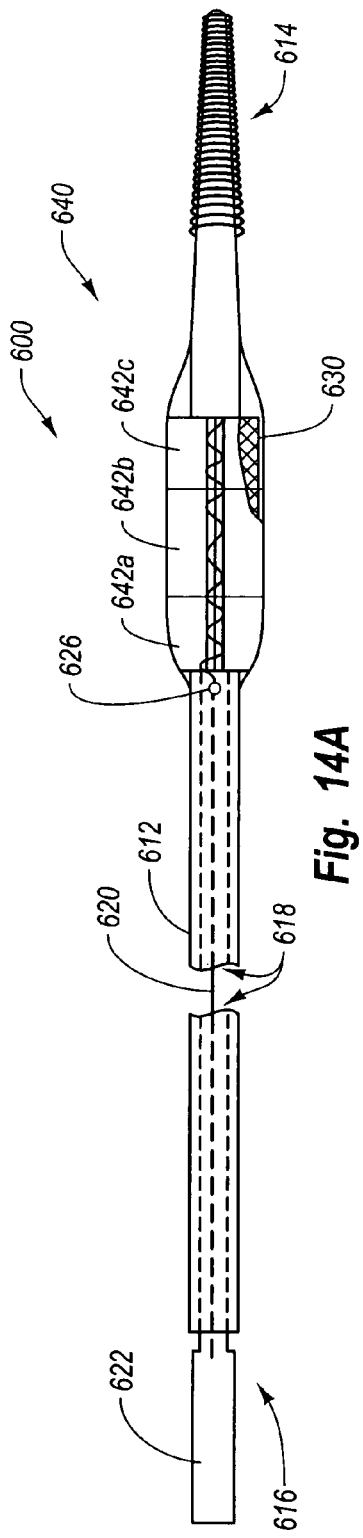
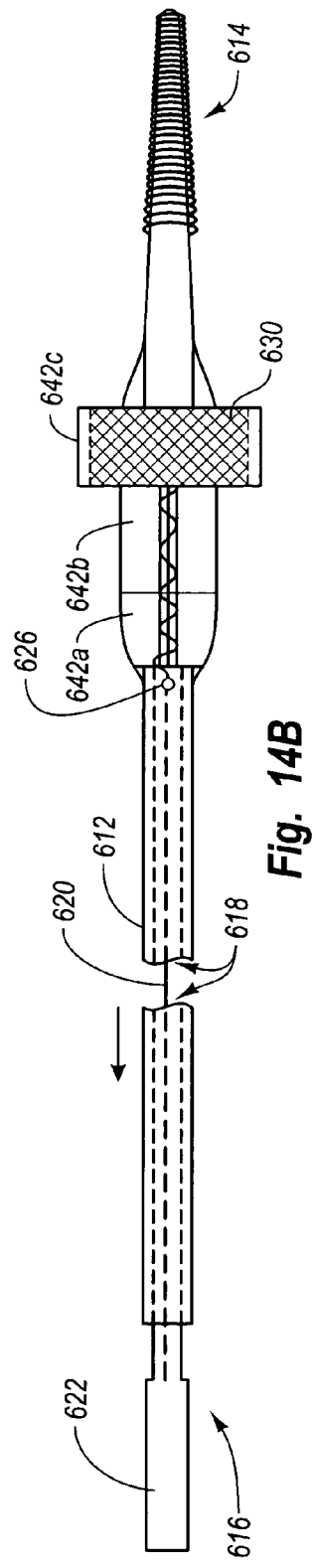
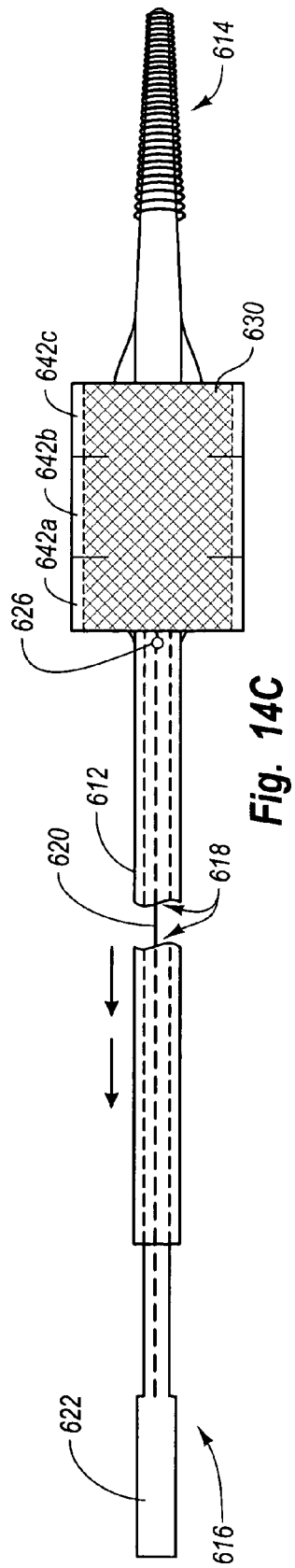

STENT DELIVERY DEVICE

CROSS-REFERENCE TO RELATED APPLICATIONS

This invention claims the benefit of and priority to U.S. Provisional Patent Application No. 60/535,324, filed on Jan. 9, 2004, entitled "STENT DELIVERY DEVICE", the entire contents of which are incorporated herein by reference.

BACKGROUND OF THE INVENTION

1. The Field of the Invention

The invention generally relates to the field of interventional procedures. More specifically, the invention relates to interventional procedures that require the placing of a stent in a body lumen, such as a body lumen of a patient or animal.

2. The Relevant Technology

Human blood vessels often become occluded or blocked by plaque, thrombi, other deposits, or material that reduce the blood carrying capacity of the vessel. Should the blockage occur at a critical place in the circulatory system, serious and permanent injury, and even death, can occur. To prevent this, some form of medical intervention is usually performed when significant occlusion is detected.

Several procedures are now used to open these stenosed or occluded: blood vessels in a patient caused by the deposit of plaque or other material on the walls of the blood vessel. Angioplasty, for example, is a widely known procedure wherein an inflatable balloon is introduced into the occluded region. The balloon is inflated, dilating the occlusion, and thereby increasing the intra-luminal diameter.

Another procedure is atherectomy. During atherectomy, a catheter is inserted into a narrowed artery to remove the matter occluding or narrowing the artery, i.e., fatty material. The catheter includes a rotating blade or cutter disposed in the top thereof. When the blade is rotated, portions of the fatty material are shaved off and retained with the interior lumen of the catheter. This process is repeated until a sufficient amount of fatty material is removed and substantially normal blood flow is resumed.

In another procedure, introducing a stent into the stenosed region to open the lumen of the vessel treats stenosis within the artery or other blood vessel. The stent typically includes a substantially cylindrical tube or mesh sleeve made from such material as stainless steel or nitinol. The design of the material permits the diameter of the stent to be radially expanded, while still providing sufficient rigidity such that the stent maintains its shape once it has been enlarged to a desired size.

To place a stent, many medical devices are typically used in combination. Typically, a small diameter guidewire is inserted through the arterial system, by way of the femoral artery, and guided to the point distal to the stenosed region.

Once the guidewire is placed, the guidewire is used as a guide for all of the other devices that are used in the procedure. These devices have an inner lumen through which the proximal end of the guidewire, which is outside of the body of the patient, is inserted. The device is then slid along the guidewire into the body, allowing the guidewire to guide the device to the required position in the vascular system. Sliding another device over the guidewire is commonly known as an exchange.

Two basic types of devices facilitate exchanging of other medical devices. The first type of device encloses a guidewire within an inner lumen of the device for the entire length of the device. The second type of device only encloses the guidewire for a small distal segment of the device, with the remainder of the guidewire exiting from the inner lumen of the device through a side hole to allow the device and the guidewire to be side by side. In both cases, control of the guidewire is paramount during the exchange as the correct positioning of the device is reliant upon maintaining the position of the guidewire; this being difficult as at least a section of the guidewire is inaccessible due to it being enclosed in the inner lumen of the device being exchanged.

Following access by the guidewire, a guide catheter is typically inserted into the artery and about the guidewire so that the tip thereof can be guided to a position just proximal to the stenosed region to be treated. This guide catheter serves the purpose of allowing other devices to rapidly be delivered to that position without each being carefully guided over the guidewire from the point of access, through the tortuous anatomy of the arterial system, to the point of intervention.

When guidewire access to the lesion is established, and if there is sufficient cross sectional area in the narrowed part of the lesion, a stent, mounted on a delivery device, is delivered over the guidewire and through the guide catheter. When correctly placed within the stenosed region, the stent will then be deployed, propping open the vessel at that point.

Various types of stents are used in these cases, but a common one requires that the stent be deployed, or expanded from a compressed state by a balloon upon which it is mounted. The balloon is inflated from the proximal end of the delivery device to a high pressure, which both opens the stenosis and embeds the stent into the inner lumen of the vessel at that point. Generally, the typical method to deliver and deploy a stent is complex, with multiple changes in the medical device slide over the guidewire and fluids to inflate the balloon deploying the stent.

Providing a stent delivery device that reduces the complexity of an interventional procedure would advance the art of stent delivery. Furthermore, reducing the number of devices used to perform a stent implanting procedure would advance the art of stent delivery.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 1 illustrates a schematic side view representation of a stent delivery device of one configuration of the present invention;

FIG. 2A illustrates a cross-sectional side view of a portion of the stent delivery device of FIG. 1;

FIG. 2B illustrates a cross-sectional side view of an alternate portion of an alternate configuration of the stent deliver device of FIG. 1;

FIG. 6 illustrates a schematic side view representation of yet another stent delivery device of the present invention having another restraining mechanism;

FIG. 7 illustrates a schematic side view representation of the restraining mechanism for the stent delivery device of FIG. 6;

FIG. 9 illustrates a schematic side view representation of yet another stent delivery device of the present invention, the stent delivery device being capable of providing embolic protection;

FIG. 10 illustrates a schematic side view representation of the stent delivery device of FIG. 9 with the embolic protection device activated;

FIG. 12 illustrates a schematic side view representation of another stent delivery device of the present invention;

FIG. 13 illustrates a schematic exploded cross-sectional view representation of the stent delivery device of FIG. 12;

FIG. 14A illustrates a schematic side view representation of yet another stent delivery device of the present invention having a segmented restraining mechanism;

FIG. 14B illustrates the stent delivery device of FIG. 14A, in which a portion of the segmented restraining mechanism is released; and FIG. 14C illustrates the stent delivery device of FIG. 14A, in which the entire restraining mechanism is released.

DETAILED DESCRIPTION OF THE EXEMPLARY EMBODIMENTS

Figure 3:
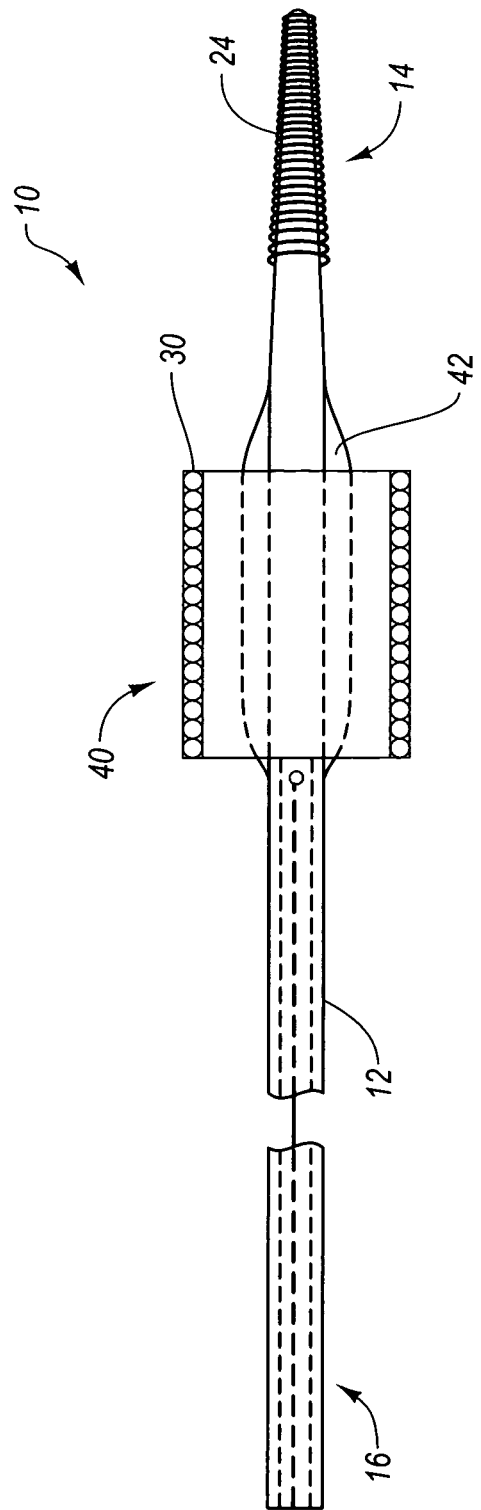
FIG. 3 illustrates a schematic side view representation of the stent delivery device of FIG. 1 with the stent deployed.

The present invention provides systems, methods, and devices that combine the functionality of a guide catheter, a guidewire, and a stent delivery device into a single device that is insertable into a body lumen. In this manner, the stent delivery device reduces the number of devices needed to deliver and position a stent, providing the possibility of decreasing the time needed to perform procedures and reducing the difficulty and complexity associated with performing a procedure. By so doing, configurations of the stent delivery device aid with decreasing the possibility of patient complications during and subsequent to the procedure.

Referring now to FIG. 1, depicted is a schematic representation of one exemplary embodiment of the present invention. As illustrated, a delivery device 10 includes a guide member 12 that supports a stent 30 and a restraining mechanism 40 that surrounds stent 30. The delivery device 10 has a distal end portion 14 and a proximal end portion 16. As used herein and the appended claims, the term "guide member" can refer to any structure that is capable of functioning as a guidewire or hypotube that can be steered through the tortuous anatomy of a patient. It will be appreciated that guide member 12 can be solid, hollow, or partially hollow depending upon design considerations.

In the illustrated configuration, guide member 12 includes a lumen 18 within which can be disposed an actuating member 20. This actuating member 20 extends from restraining mechanism 40 toward proximal end portion 16 and terminates at a handle 22 that slidable cooperates with proximal end portion 16 and optionally a portion of lumen 18. It will be understood that actuating member 20 can also form part of restraining mechanism 40 such that the restraining mechanism includes the structures or elements that surround the stent and also the structures or elements that cause such structures or elements that surround stent 30 to release the force they apply upon stent 30.

Distal end portion 14 of delivery, device 10 includes a tip 24 that can be configured for percutaneous insertion into a body lumen. This tip 24 can be integrally formed with guide member 12 or alternatively have a form of a separate structure that is mounted within a distal end of lumen 18. In either case, tip 24 can be an atraumatic and/or flexible tip that aids in positioning and steering of delivery device 10 through the tortuous anatomy of the patient. This tip 24, therefore, can include a flexible coil that terminates with an atraumatic portion, such as a solder ball or other mechanism for forming an atraumatic distal end of tip 24.

Generally, tip 24 can have a variety of other configurations so long as tip 24 is flexible and optionally shapeable. Furthermore, tip 24 may be radiopaque to allow a physician or clinician to observe the location of tip 24 using appropriate devices, such as a fluoroscopic device or X-ray device, as the steerable position delivery device 10. Materials that facilitate or provide radiopacity may include, but not limited to, platinum, alloys of platinum, gold, or combinations thereof, metals, alloys, plastic, polymer, synthetic material, combinations thereof, or other materials that provide an appropriate radiopaque signature, while capable of being shaped by a physician or clinician. Alternatively, tip 24 can be a polymer that is mixed, filled, or coated with an appropriate radiopaque material, such as, but not limited to, barium sulphate, bismuth subcarbonate, titanium dioxide, or combinations thereof.

Illustratively, guide member 12 of delivery device 10 can have an outside diameter of between about 0.010 inches to about 0.650 inches and an inside diameter or diameter of lumen 18 from about 0.004 inches to about 0.55 inches. Additionally, guide member 12 can be fabricated from a variety of different materials. For example, guide member 12 can be fabricated from a shaped memory metal such as Nitinol, steel, stainless steel, metals, metal alloys, composites, plastic, polymers, synthetic materials, such as, but not limited to, PEEK, Rydel, shaped memory materials or combinations thereof.

Shape memory materials suitable for use in fabrication of guide member 12 include, but are not limited to, shape memory polymers, shape memory metals, such as NiTiNOL, and other materials both natural and synthetic. Several shape memory polymer materials may be suitable for fabrication of guide member 12. These materials include but are not limited to: polyurethane; polycycloocetene; cross-linked polyethylene; thermoplastics such as shape memory polyurethanes, polyethylene, polynorborene polymers and copolymers and blends thereof with styrene elastomer copolymers, such as Kraton, and cross-linked transpolyoctylene rubber; cross-linked polyisoprene; styrene butadiene copolymers; bioabsrobable shape memory polymers such as polycaprolactone, coplymers, and/or PLLA PGA copolymers; PMMA; Azo-dyes, Zwitterionic and other photo chromatic materials.

Additionally, guide member 12 can have the configuration of a braid-reinforced polymer tube or a rigid polymer tube. The guide member 12 can also be covered with one or more coatings. For instance, and not by way of limitation, guide member 12 can include one or more coatings that improve lubricity, reduce platelet aggregation, or have anti-thrombogenic properties. In addition to the above, guide member 12 can include one or more hydrophilic coatings, heparinized coatings, Polytetrafluoroethylene (PTFE) coatings, silicone coatings, combinations thereof, or other coatings that may aid with positioning guide member 12 and/or preventing damage to the body lumen.

Optionally, guide member 12 may include one or more cuts, slits, grooves, lattice structures, or other structures that provide flexibility to all or a portion of guide member 12. These cuts, slits, or grooves can be fabricated using machining processes performed using a laser or conventional machining process, including, but not limited to, hydro-machining, grinding, end milling, slitting saws, abrasive saws, electrical discharge machines, combinations thereof, or other machining processes capable of creating the grooves, cuts, or slits.

Mounted to an outside surface of guide member 12 is stent 30. Stent 30 can have various configurations. In the exemplary configuration of FIG. 1, stent 30 is a self-expanding stent that automatically opens following removal of the restraining force applied by restraining mechanism 30. The opening of stent 30 can be due to the materials forming stent being biased to or having a "memory" for a predefined configuration. Self-expanding stents are known in the art, such as laser-cut or etched tubes or sheets made from nitinol or other metals or braided nitinol or metal stents.

Although reference is made to use of a self-expanding stent, one skilled in the art will understand that balloon expandable stents can also be used. In such a case, guide member 12 can be modified to include a dilation balloon mounted to the outer a surface of guide member 12. With this configuration, an inflation tube would extend from the dilation balloon toward proximal end portion 16 of guide member 12, either within or without of lumen 18. Various stents may be used with the present invention, so long as the stent can be reduced in size to surround guide member 12.

Surrounding stent 30 is restraining mechanism 40. This restraining mechanism 40 is one example of one structure capable of performing the function of a means for limiting movement of the stent. It is also an example of restraining means for restraining a self-expanding medical device. Other structures capable of performing these functions will be known to those skilled in the art.

In this exemplary configuration, restraining mechanism 40 is a restraining member in the form of a sleeve 42. Sleeve 42 can be adapted to retain or maintain stent 30 in a restrained or closed configuration. Sleeve 42 can include a first end 44 and a second end 46 that are in close proximity one to another while sleeve 42 restrains stent 30 and which are disposed one from another when stent 30 is deployed. Sleeve 42 can attach to guide member 12 at either a proximal or distal end of sleeve 42 so that sleeve 42 can be removed from the body lumen following deployment of stent 30. In other configuration, sleeve 42 can attach to stent 30 and remain within the body lumen following deployment of stent 30.

Sleeve 42 can be fabricated from various types of materials so long as sleeve:. 42 is capable of securely retaining stent 30. For instance, sleeve 42 can be fabricated from heat shrink synthetic material, including but not limited to, low-density polyethylene (LDPE), polyethylene terphthalate (PET), Polytetrafluoroethylene (PTFE), fluorinated ethylene propylene (FEP), polyethylene (PE), polyurethane (PU), silicone tubing, and other suitable polymers or synthetic materials.

Actuating member 20 cooperates with sleeve 42 and maintains first end 44 and second end 46 in contact or in close proximity one with another as the combination of actuating member 20 and sleeve 42 prevent stent 30 from expanding. The actuating member 20 passes through portions of sleeve 42 close to first end 44 and second end 46. The combination of actuating member 20 and sleeve 42 prevent expansion of stent 30 until actuating member 20 is moved in a proximal direction and removed from its engagement with sleeve 42. In the illustrated configuration, actuating member 20 passes through portions of sleeve 42, or is stitched through portions of sleeve 42, in such a manner that first end 44 and second end 46 remain in close proximity one with another until actuating member 20 is moved in a proximal direction and unstitched from sleeve 42.

It will be understood that actuating member 20 can pass through other portions of sleeve 42 to achieve the desired result of preventing movement of sleeve 42, and that would otherwise allow stent 30 to be deployed. For instance, actuating member 20 can pass through portions of sleeve 42 that are disposed between ends 44 and 46, with ends 44 and 46 being wrapped at least partially around the remaining portions of sleeve 42 following stitching of actuating member 20 with sleeve 42. In this manner, additional restraining forces can be applied to stent 30.

It will be understood that various other configurations of restraining mechanism 40 and restraining members are possible. In another configuration, sleeve 42 is separated into two or more sub-sleeves, through which passes actuating member 20. These sub-sleeves can have a shorter length than sleeve 42, such that two or more sub-sleeves can be used to constrain stent 30. For instance, one sub-sleeve can be disposed at a distal end of stent 30 and one sub-sleeve disposed at a proximal end of stent 30. The actuating member 20 can pass through both sleeves. Alternatively, two or more separate actuating members can be used to constrain the sleeves, and hence stent 30. It will be understood that the location of these sub-sleeves can be varied as well as the number needed to constrain stent 30.

In a similar vein, restraining mechanisms or members can utilize one or more sub-sleeves in combination with one or more features or structures of stent 30, to prevent expansion or deployment of stent 30. For instance, a sleeve having a length shorter than the length of restraining mechanism 40, yet which substantially extends the length of stent 30, can be disposed about a distal end of stent 30. Passing through this sleeve, and one or more hoops or loops formed in stent 30, is actuating member 20. The location of the hoops and loops in stent 30 are selected so that passing actuating member 20 therethrough prevents stent 30 from opening. Consequently, a combination of restraining mechanisms, members, and techniques can be used to maintain a single stent 30 in a closed configuration.

In another configuration, sleeve 42 can be a generally cylindrical member that surrounds stent 30, with actuating member 20 attached to at least a portion of sleeve 42. Movement of actuating member 20 in a proximal direction results in this latter sleeve sliding relative to stent 30, thereby allowing stent 30 to expand. It will be understood that other restraining members or mechanisms can be used, some of which are described hereinafter. Further, embodiments of the delivery device of the present invention can use any combination of any of the restraining mechanisms, members, techniques or methods to prevent stent 30, and the struts (which will be discussed hereinafter) from being deployed or moving in a desired manner. It will be understood that the combination of actuating member 20 with restraining mechanism 40 is another structure capable of performing the function of means for restraining a stent 30, or restraining means for controlling stent 30 expansion.

With continued reference to FIG. 1, actuating member 20 extends from sleeve 42, travels along an exterior of guide member 12, and passes through an aperture 26 in guide member 12. Actuating member 20 continues to travel within lumen 18 of guide member 12 until it reaches proximal end portion 16 of delivery device 10. It will be appreciated that in other embodiments, actuating member 20 may remain external to lumen 18 of guide member 12.

Actuating member 20 can be fabricated from various materials, and can have various configurations, so long as it is capable of performing the function of releasing the restraining force applied by sleeve 42. For example, actuating member 20 can be fabricated from plastics, polymers, metals, composites, alloys, synthetic materials, and combinations thereof.

As mentioned above, actuating member 20 terminates at handle 22. With reference to FIG. 2A, handle 22 is shown cooperating with lumen 18 of guide member 12. Handle 22 includes a distal end 50 configured to be mounted to and cooperate with guide member 12 at proximal end portion 16 of delivery device 10. A proximal end 52 of handle 22 is configured to be grasped by a physician or clinician during a procedure. The distal end 50 acts as a protrusion from proximal end 52; lumen 18 of guide member 12 receiving distal end 50.

Handle 22 has substantially the same outside diameter as guide member 12, thereby allowing other medical components to be exchanged thereover. Actuating member 20 can be mounted to distal end 50 of the handle 22 through use of adhesives, interference fit connections, fasteners, combinations thereof, or other manner of attaching one member to another member.

Handle 22 can be adapted to be displaced in a distal direction to deploy stent 30 (FIG. 1). To aid with positioning handle 22, distal end 50 can optionally include protrusions 54 that mate with complementary indentations 56 formed in proximal end portion of guide member 12. The protrusions 54, and corresponding indentations 56, provide an indication of the relative position of handle 22 relative to proximal end of guide member 12, and hence the degree of deployment of stent 30 (FIG. 1). As handle 22 is displaced in a distal direction, protrusions 54 mate with indentations 56.

Although reference is made to one manner of indicating the particular location of stent 30 (FIG. 1), one skilled in the art can identify a variety of different embodiments. For instance, a plurality of indentations and/or protrusions can be included within handle 22 and guide member 12 to control the distance which handle 22 and, consequently, stent 30 (FIG. 1) is displaced. In another configuration, a wall or stop formed in handle 22 can mate with a complementary wall formed in guide member 12, to prevent excessive longitudinal displacement in the distal direction. In still another configuration, a combination of one or more walls or stops in handle 22 and guide member 12 can be used. In still another configuration, distal end 52 of handle 22 can be tapered and cooperate with a taper formed in the proximal end portion of guide member 12. The complementary tapers control the longitudinal displacement of handle. 22 relative to the proximal end portion of guide member 12. In still other configurations, a combination of indentations, protrusions, walls, stops, threads, or tapers can be used. Various other manners are known to control the distance traveled by handle 22, while indicating the position of stent 30 (FIG. 1).

An alternate configuration of the handle of FIG. 2A is depicted in FIG. 2B, as referenced by numeral 22b. Handle 22b cooperates with a guide member 12b so that instead of handle 22 being received within lumen 18 of guide member 12, handle 22b receives a proximal end 13b of guide member 12b. The handle 22b includes a cavity 54b formed by walls 56b that extend from a distal end 50b of handle 22b towards a proximal end 52b of handle 22b. The walls 56b of cavity 54b are configured to interference fit with the outer surface of proximal end 13b and limit movement of handle 22b relative to guide member 12b. With proximal end 13b having a cross-sectional dimension that is smaller than the cross-section dimension of guide member 12b extending towards distal end portion 14 (FIG. 1), the cross-sectional dimensions of handle 22b and guide member 12b substantially match. This matching enables other devices to be exchanged over handle 22b and guide member 12b.

As with handle 22, actuating member 20 can be mounted to handle 22b. Instead of mounting to a distal end of the handle, however, actuating member 20 mounts to proximal end 52b within cavity 54b through use of adhesives, interference fit connections, fasteners, combinations thereof, or other manner of attaching one member to another member.

The illustrated proximal end 13b and cavity 54b each generally have uniform dimensions along their lengths to facilitate sufficient interference contact to maintain attachment of handle 22b to guide member 12b until a physician grasps and removes handle 22b and the attached actuating member 20. It will be understood that there are various manners to achieve the desired interference contact. For instance, in one configuration, proximal end 13b and/or the walls forming cavity 54b can include one or more protrusions and complementary indentations, such as those described with respect to FIG. 2A. In another configuration, one or both of proximal end 13b and cavity 54b have non-uniform dimensions along their lengths. For instance, proximal end 13b can have a tapered configuration, a stepped configuration, combinations thereof, or other dimensions that facilitate interference contact with the wall of handle 22b that form cavity 54b. Similarly, the walls of handle 22b can have a tapered configuration, a stepped configuration, combinations thereof, or other dimensions that facilitate interference contact with proximal end 13b of guide member 12b. So long as the configurations of cavity 54b and proximal end 13b are complementary and/or allow a releasable interference fit or contact between wall 56b forming cavity 54b and proximal end 13b any configuration of cavity 54b and proximal end 13b are possible.

Referring now to FIG. 3, illustrated is device 10 with stent 30 in a deployed configuration. To reach this particular point, device 10 has been positioned with a lumen of the patient, such as with any of a variety of blood vessels of the patient. Upon positioning device 10 in the desired location, a physician or clinician can move handle 22 relative to the proximal end portion of guide member 12. By so doing, handle 22 moves actuating member 20 in a proximal direction. Moving actuating member 20 in a proximal direction removes actuating member 20 from engagement with sleeve 42. Stated another way, as actuating member 20 moves in a proximal direction, a distal end of actuating member 20 unstitches sleeve 42, thereby allowing stent 30 to expand. When the actuating member is released, a portion of the restraining mechanism, i.e., sleeve, may be disposed between the vessel wall and the expanded stent. The handle 22, with attached actuating member 20 can be either completely removed from engagement with guide member 12, or may remain in contact with guide member 12, but disengaged from restraining mechanism 40.

FIGS. 4 through 8 illustrate alternative embodiments for restraining mechanism 40. It will be appreciated that many features of the delivery devices depicted in FIGS. 4 through 8 are substantially similar in structure and function as for delivery device 10. Consequently, features and functions of one embodiment of the present invention are applicable to other embodiments of the present invention. Further, each of these configurations of a restraining mechanism, whether alone or in combination with an actuating member and/or one or more other restraining mechanisms are examples of structures capable of performing the function of means for restraining a stent 30, or restraining means for controlling stent 30 expansion.

Figure 4:
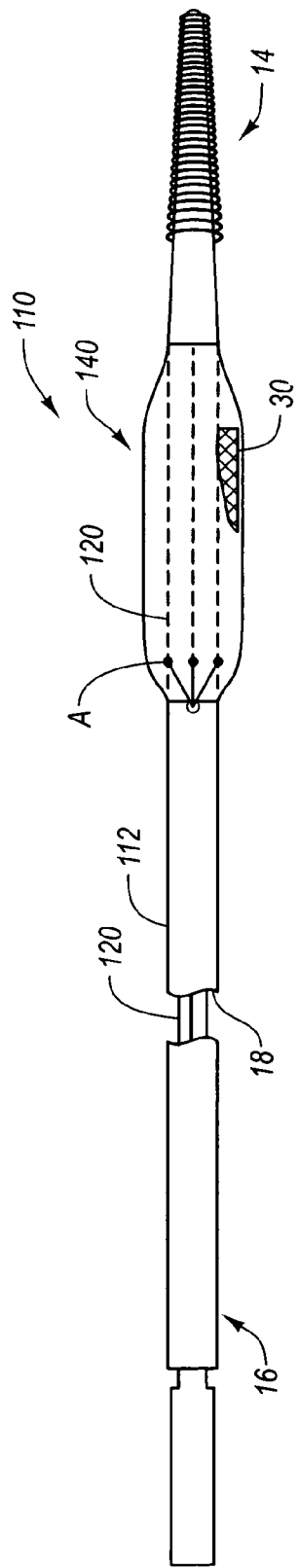
FIG. 4 illustrates a schematic side view representation of another stent delivery device of the present invention having another restraining mechanism.
Figure 5:
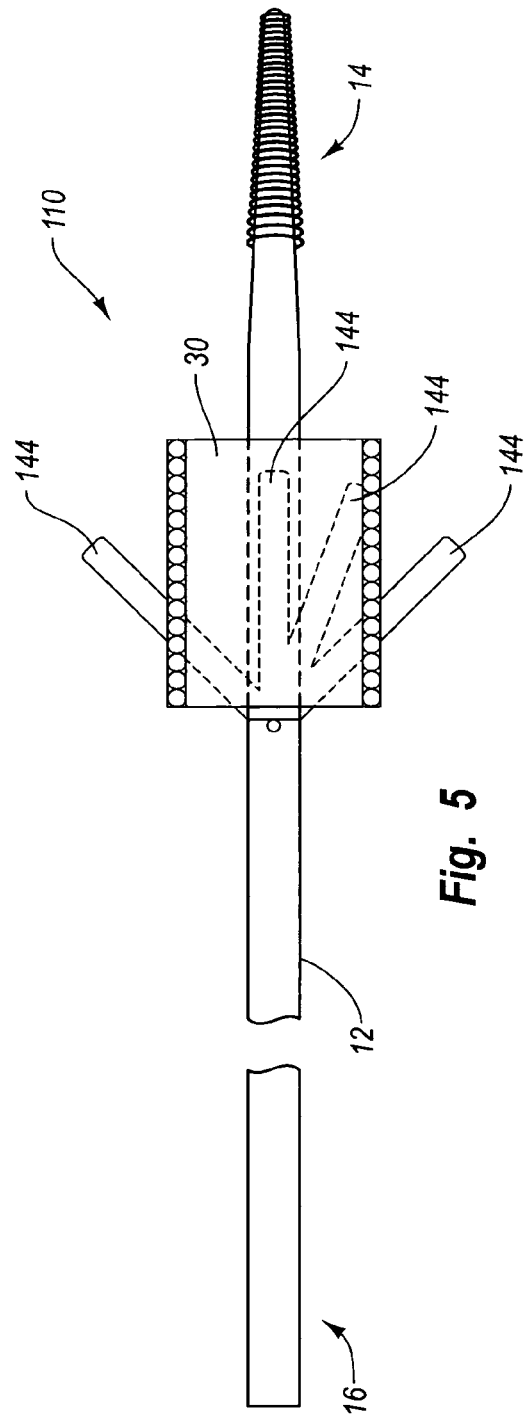
FIG. 5 illustrates a schematic side view representation of the another stent delivery device of the present invention having another restraining mechanism.

Referring now to FIGS. 4 and 5, another illustrative embodiment of a delivery device 100 of the present invention is depicted. As shown, a guide member 12, which can be similar to the other guide members described herein, has a distal end portion 14, a proximal end portion 16, and a lumen 18 extending from proximal end portion 16 toward distal end portion 14. A restraining member 140 restrains stent 30 mounted to guide member 12. In this configuration, restraining mechanism 140 is a sleeve 142 surrounding stent 30, which forces stent 30 into a closed or contracted position.

Disposed within the restraining member 140 and guide member 12 can be one or more actuating members 120. Actuating members 120, optionally form part of the restraining mechanism or member 140, and can fixably or releasably attach to guide member 12 at a location proximal to the proximal end of stent 30, identified by letter A. Actuating members 120 extend from location A beneath sleeve 142, and then extend proximally along the outside of sleeve 142 to the proximal end of the restraining member 140 or sleeve 142.

Since one end of each actuating member 120 is located at the proximal end of sleeve 142, whether forming part of sleeve 142, attached to sleeve 142, attached to guide member 12, or combinations thereof, displacing actuating member 120 in the proximal direction causes actuating member 120 to preferentially separate sleeve 142 into one or more flanged portions 144, illustrated in dotted lines in FIG. 5. Thus, when the actuating member 120 is moved in the proximal direction, stent 30 is released, as illustrated in FIG. 5.

With reference to FIGS. 4 and 5 together, to operate actuating members 120, a proximal end (not shown) of actuating member 120 extends to proximal end portion 16 of guide member 12, either within or without lumen 18 of guide member 12. Actuating members 120 can extend to handle 22 (FIG. 1), as described herein and understood by one skilled in the art in light of the teachings contained herein. The actuating member 120 can be displaced in the proximal direction relative to guide member 12 as handle 22 (FIG. 1) moves proximally to guide member 12. By so doing, the restraining force applied by restraining member 140 is released, and stent 30 is deployed.

The restraining member 140 can be formed from a variety of different materials, so long as the material is sufficiently strong to secure stent 30, while being configured to preferentially separate under the action of actuating members 120. For example, such a sleeve 142 can be fabricated from heat shrink synthetic material, including but not limited to, low-density polyethylene (LDPE), polyethylene terphthalate (PET), Polytetrafluoroethylene (PTFE), fluorinated ethylene propylene (FEP), polyethylene (PE), polyurethane (PU), or silicone tubing.

The one or more actuating members 120 can be formed from a variety of different materials, so long as the material used is sufficiently strong to allow displacing of actuating member 120 proximally without breaking the same. For example, actuating members 120 can be fabricated from plastics, polymers, metals, composites, alloys, synthetic materials, and combinations thereof.

Instead of using actuating members 120, embodiments of the present invention can employ various other techniques or mechanisms to preferentially separate sleeve 142. For example, restraining member 140 or sleeve 142 can have dissolvable chemical bonds which dissolve due to a chemical reaction with the fluid in the body lumen, within which the delivery device 10 is disposed. These bonds can be broken by applying resistive heating, ultrasonic, or radio frequency energy to actuating members 120 and/or region of the body lumen containing device 100, or by preferential tearing or cutting regions or zones where the material has a weaker strength than other regions or zones of the sleeve, or combinations thereof.

Referring now to FIG. 6, depicted is another embodiment of a delivery device 200, having another embodiment of a restraining mechanism or member 240. In this embodiment, restraining mechanism member 240 is in the form of a sleeve, which is adapted to surround stent 30, and apply a restraining force against stent 30 to maintain stent 30 in a restrained configuration. The restraining member 240 functions in a similar manner to a hinge with an actuating member 220, which function or act as the pin to maintain the hinged portions of restraining member 240 in a configuration that retains or restrains a portion of the guide member 12.

In particular, FIG. 6 shows that restraining member 240 is a sleeve 242 having a plurality of channels 244a-244n. These channels 244a-244n are adapted to receive actuating member 220. Both a first side 246 and a second side 248 of sleeve 242 are formed with some of channels 244a-244n, only 244a-244n being identified. In a closer view, FIG. 7 shows that these channels 244a-244n are formed with portions of sleeve 242, in an alternating fashion. More specifically, sleeve 242 includes one or more extensions (or tongues) 250a-250n that are wrapped around actuating member 220, which passes through channels 244a-244n. A first side 246 forms one or more of channels 244a-244n with one or more tongues 250a-250n, while a second side 248 forms one or more of channels 244a-244n with one or more tongues 250a-250n.

Thus, as shown in FIG. 7, channels 244a, 244c, 244e, 244g, 244i, 244k and 244m are formed by first side 246, while channel 244b, 244d, 244f, 244h, 244j, 244l, and 244n are formed by second side 248. By passing actuating member 220 through channels 244a-244n in sequential order, so that actuating member 220 passes through a channel on first side 246, and subsequently a channel on second side 248, first side 246 is coupled to second side 248, and sleeve 242 therefore restrains stent 30 and selectively prevents stent 30 from opening until actuating member 220 is removed from channels 244a-244n.

Figure 8:
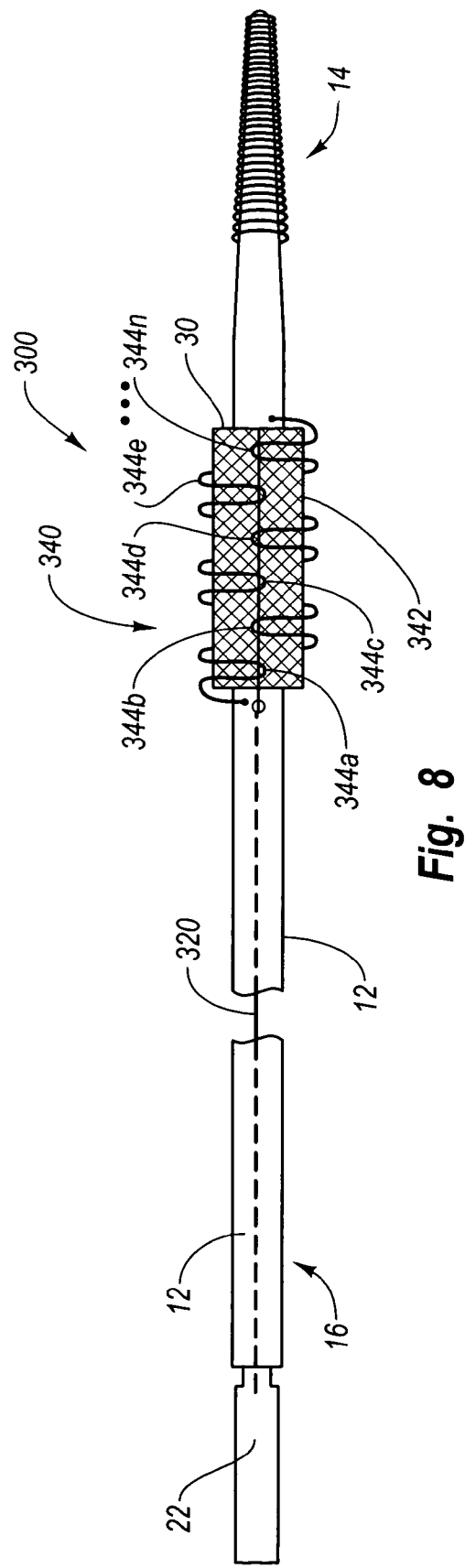
FIG. 8 illustrates a schematic side view representation of still yet another stent delivery device of the present invention having another restraining mechanism.

Referring now to FIG. 8, another delivery device 300 has another embodiment of a restraining member or mechanism 340, in accordance with the present invention. The restraining member 340 includes a ligature 342 mounted to a portion of delivery device 300, such as, but not limited to guide member 12 and/or stent 30. The ligature 342 forms a number of hoops 344a-344n. The one or more of hoops 344a-344n are adapted to receive an actuating member 320, which is optionally part of restraining member or mechanism 340. The actuating member 320 is disposed within hoops 344a-344n so that ligature 342 restrains expansion of stent 30 mounted to guide member 12. In particular, actuating member 320 can be removed from hoops 344a-344n to allow stent 30 to be deployed as handle 22 is moved proximally relative to guide member 12.

Ligature 342 may be made from metallic or polymer wires, or other materials that can be manipulated to form hoops through which an actuating member may pass. Optionally, ligature 342 can be adapted to expand outwardly either under the influence of stent 30, or due to a biasing force applied or incorporated within ligature 342, by the configuration and/or material of the cord, the hoops, and/or the restraining member.

Ligature 342 can be attached to guide member 12 and/or stent 30 through various attachment mechanisms. For instance, ligature 342 can be attached to guide member 12 and/or stent 30 through adhesives, mechanical fasteners, securing loops, or other similarly secure manner. Alternatively, ligature 342 may be attached directly to, or form part of actuating member 320, and hence be removed when actuating member 320 is moved in a proximal direction.

Referring now to FIG. 9, another embodiment of a stent delivery device, identified by reference number 400, is capable of both delivering a stent to a desired location, and providing embolic protection. As known to those skilled in the art, during an interventional procedure, there is the possibility of embolic particles breaking off, flowing downstream, and causing potentially adverse events. Devices are emerging that are designed to catch or filter these particles to prevent their down-stream flow or to occlude the vessel during the intervention. These devices are known as embolic protection devices.

Current embolic protection devices are delivered to a lesion in a sheath, distal to the point of intervention. This involves crossing the lesion with a large-diameter, relatively stiff, device before the embolic protection device is in place. This can result in the occurrence of an embolic event resulting in the release of particles at the legion that may flow downstream and cause an embolic current. Once in place, the sheath must then be removed, allowing the filter to be deployed in the vessel. After the device is deployed, balloons, stents, or other therapies of choice may be deployed to treat the area of interest. When the procedure is completed, the embolic protection device is captured by another catheter, which is exchanged over the embolic protection device, capturing any potential embolic material within. This procedure complicates providing stenting and other procedures.

In contrast with conventional technology, the device 400 eliminates and overcomes deficiencies by allowing quicker, safer and easier protection and stenting procedures. This is achieved through a stent delivery device that includes the functionality, and associated structures, of embolic protection.

With continued reference to FIG. 9, delivery device 400 has a filter assembly 450 disposed distally of guide member 412. Consistent with teachings of the present invention, delivery device 400 has guide member 412 that supports a stent 430, and a restraining mechanism 440. The stent 430 and restraining mechanism 440 can have similar configurations to the other stents and restraining mechanisms described herein. As such, restraining mechanism 440 cooperates with an actuating member 420, which extends from a handle 422 disposed at a proximal end portion 416 of guide member 412 toward restraining mechanism 440. In contrast to other embodiments or configurations, actuating member 420 also extends distally from restraining mechanism 440, and cooperates with filter assembly 450, which is disposed at a distal end portion 414 of delivery device 400 and mounted to a distal end of guide member 412.

The filter assembly 450 can provide embolic protection during use of device 400. As depicted in FIGS. 9, filter assembly 450 has a low profile to facilitate insertion of the same within a body lumen. The filter assembly 450 can include a filter basket 452 and a filter 454. Before deployment, filter 454 can be disposed inside filter basket 452, can surround filter basket 452, or can be employed in some combination thereof. The filter 454 can be adapted to capture embolic particles or material that may become dislodged during a procedure associated with delivery device 400, or optionally other procedures, such as when delivery device 400 is removed from guide member 412 and/or filter assembly 450. Consequently, filter 454 can optionally float within a body lumen upon being deployed, with a distal end of filter 454 floating in the body lumen and the proximal end of filter 454 being coupled to filter basket 452. In another configuration, an atraumatic tip extends from a body 458 of filter basket 452 through filter 454, with a distal end of filter 454 being coupled to a portion of the atraumatic tip.

The filter 454 can be fabricated from a variety of different materials, such as, but not limited to, a woven or braided plastic or metallic mesh, a perforated polymer film, shaped memory material, a mesh of shaped memory material or polymers, combinations thereof, or other material that is capable of capturing material within flowing blood, while allowing the blood to flow through the pores or apertures thereof.

In addition to the above, filter 454 can be coated with a hydrophilic coating, a heparinized coating, a Polytetrafluoroethylene (PTFE) coating, a silicone coating, combinations thereof, or various other coatings as know or desired by one skilled in the art in light of the teaching contained herein. Generally, filter 454 can be fabricated from a variety of materials so long as filter 454 is capable of being packed within filter basket 452, and optionally float in the blood flow or stream passing through the body lumen within which it is inserted, and is bio-compatible.

Filter 454 can have a variety of differently sized pores ranging from about 50 microns to about 200 microns, from about 60 microns to about 180 microns, or from about 75 microns to about 150 microns. For instance, the pores can have a variety of different configurations, such as but not limited to circular, oval, polygonal, combinations thereof, or other configurations known to one skilled in the art. In one configuration, therefore, filter 454 can include pores that are differently sized and configured.

Consequently, a major or minor axis of each pore can have a variety of different sizes ranging from about 50 microns to about 200 microns, from about 60 microns to about 180 microns, or from about 75 microns to about 150 microns. Generally, the pore size can vary as needed, so long as the pores are sized so that the pores do not compromise blood flow through the filter; i.e., prevent blood flowing through the filter, and collect material that could potentially occlude smaller downstream vessels, potentially blocking blood flow to tissue or result in stroke or infarction.

The filter basket 452 supports filter 454 following deployment of filter 454. The filter basket 452 can include a plurality of struts 456 that extend from body 458. Struts 456 of filter basket 452 are adapted to extend outwardly to position filter 454 within the body lumen. The struts 456 can attach to one or more of a proximal end, a distal end, and/or between a proximal end and a distal end of filter 454. A strut 456a can optionally function as an atraumatic tip 460, with struts 456a forming at least a portion of the core wire of atraumatic tip 460. As shown, strut 456a may also be covered with a flexible and optionally radiopaque coil. In another configuration, the atraumatic tip 460 is formed of a separate member that attaches or couples to body 458, such that this separate member and body 458 have substantially the same longitudinal axis. In this latter case, atraumatic tip 460 passes through a portion of filter 454, and is optionally attached to filter 454.

Each strut 456 can include a distal portion, a proximal portion, and an intermediate portion disposed between the distal portion and the proximal portion of the filter 454. In particular, struts 456 may attach to filter 454 on the exterior of filter 454, on the interior of filter 454, along the edge of filter 454, through filter 454, or through any combination of the preceding. To provide additional surface area to connect each strut 456 to filter 454, each strut 456 can be configured so that its distal portion has a cross-sectional dimension larger than the intermediate portion. Stated another way, the distal portion can have a larger surface area than the intermediate portion. The large cross-sectional area provided by such a distal portion provides sufficient area for bonding the given strut 456 to filter 454. Such a configuration creates a strong bond between the strut 456 and filter 454.

Similarly, each strut 456 can be configured so that the proximal portion has a cross-sectional dimension larger than the intermediate portion, while optionally having a similar, larger, or smaller cross-sectional dimension than the distal portion. By having a large cross-sectional dimension and hence large surface area, each strut 456 can apply a greater biasing force to extend strut 456 outwardly, which helps deploy filter 454. In particular, by varying the cross-sectional dimensions of the distal portion, the intermediate portion, and/or the proximal portion, varies the degree of bias exerted by each strut 456, when forcing the distal portion of the filter 454 toward the wall of a blood vessel. Alternatively, the biasing force can also be changed through optionally varying the length of each strut 456 and/or changing the curvature of each strut 456.

Although reference is made herein to one or more of struts 456 having the above-referenced configurations, one skilled in the art can appreciate that each strut 456 can have a generally uniform width along its length. Further, each strut 456 can optionally be configured differently so that each strut 456 can have similar or dissimilar biasing forces compared to others struts 456 of the same delivery device. Through varying the biasing forces, the delivery device can be used for a variety of different procedures or configurations.

Further, although reference is made herein to struts 456 being associated with filter assembly 450, it is also contemplated that struts 456 can form distal end 414 of guide member 412, thereby eliminating the need for a separate filter basket that attaches or mounts to distal end 414 of guide member 412. In such a case, distal end 414 can be cut such that a number of struts are formed at the end thereof, with one of the struts optionally having the form of an atraumatic tip, or the form to have the flexibility and other characteristics associated with an atraumatic tip. The struts 456 formed at distal end 414 would be biased to expand outwardly.

The filter 454 would thus be attached to the struts 456 in a similar manner to that described herein, with the restraining mechanisms and members applying a restraining force against the struts 456, and hence distal end 414 of guide member 412. When one of the cut struts is to function as the atraumatic tip, an atraumatic tip can be mounted within the lumen of guide member 412 and extend outwardly.

Struts 456 can be formed from shaped memory materials, stainless steel, metals, alloys, composites, plastics, polymers, synthetic materials, or combinations thereof. Each strut 456 can have a generally straight distal portion, proximal portion, and/or intermediate portion. Alternatively, each strut 456 can have a generally curved distal portion, proximal portion, and/or intermediate portion. In still another configuration, each strut 456 can have a combination of one or more straight and/or one or more curved portions.

The filter 454 can be attached to struts 456 of filter basket 452 in a variety of ways. For instance, filter 454 can be attached through adhesives, solvent bonding, thermal bonding, mechanical connections, or combinations thereof. Further, the distal end of two or more struts 456 can include a hole through which strands of filter media can be passed and attached to struts 456. Alternatively, the strands can be tied in a knot, folded back upon filter 454, and affixed to filter 454. Various other manners exist for coupling or connecting filter 454 to filter basket 452.

Optionally, filter assembly 450 includes a number of radiopaque bands and/or markers affixed to a variety of positions on filter assembly 450. For instance, bands, markers or other means for radiopacity can be included upon filter 454, filter basket 452 and/or struts 456. In other configurations, the delivery device generally includes means for radiopacity at one or more positions to aid with viewing the position of the delivery device, and/or related components.

As illustrated, actuating member 420 surrounds struts 456 to restrain struts 456. The actuating member 420 can pass through one or more holes formed in struts 456 and maintain the struts 456 in a closed position until action member 420 is removed. Alternatively, a restraining mechanism or member, such as those described herein, cooperate with actuating member 420 to restrain struts 456. Further, two or more different restraining mechanisms and/or members can be used to restrain portions of filter assembly 450 and/or stent 430.

By way of example and not limitation, a restraining member or mechanism, having a similar configuration to the restraining member discussed with respect to FIG. 8, can surround struts 456, with the actuating member 420 passing through respective hoops of ligature 342. Alternate restraining mechanism or members usable to restrain struts 456 are described herein and in co-pending U.S. patent applications Ser. No. 10/186,275, filed Jun. 28, 2002, entitled "Methods, Systems and Devices for Providing Embolic Protection and Removing Embolic Material", U.S. patent application Ser. No. 10/290,099, filed Nov. 7, 2002 and entitled "Methods, Systems and Devices for Delivering Stents,", and U.S. patent application Ser. No. 10/464,725, filed Jun. 18, 2003 and entitled "Stent Delivery Device with Embolic Protection", the disclosures of which applications are incorporated herein by reference.

It will be understood that actuating member 420 can also form part of the restraining mechanism or member, such that the restraining mechanism or member includes the structures or elements that surround the stent 430, or struts 456. The actuating member 420 can also comprise the structures or elements that surround and release the restraining force applied upon the stent or struts.

Turning to FIG. 10, device 400 is shown in a partially actuated position. As shown, a handle 422 has been partially moved in a proximal direction, thereby releasing any optional restraining members or mechanism upon struts 456 of filter assembly 450. In particular, moving handle 422 proximally removes actuating member 420 from within the holes (or eyelets) formed in struts 456, thereby allowing struts 456 to expand, and hence to deploy filter 454.

Figure 11:
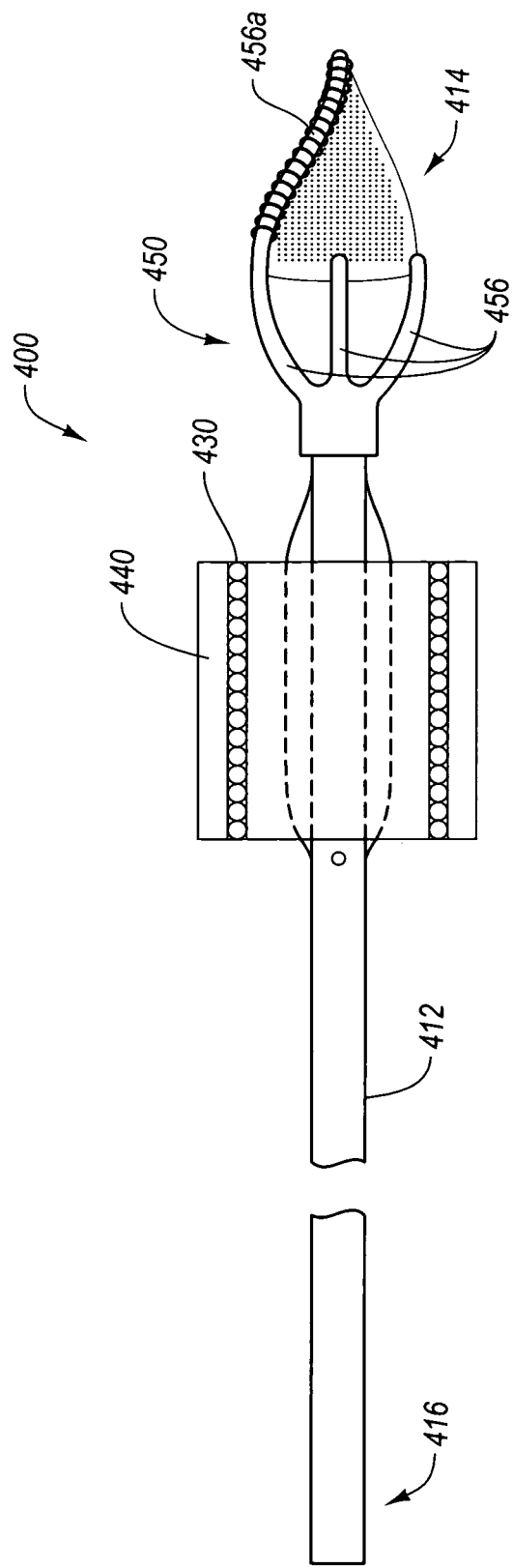
FIG. 11 illustrates a schematic side view representation of the stent delivery device of FIG. 9 with the stent activated.

Following deploying filter 454, continuing to move actuating member 420 proximally releases the restraining forces applied by restraining mechanism 440. Resultantly, stent 430 is deployed from within restraining mechanism 440, as illustrated in FIG. 11. Therefore, two restraining mechanisms can optionally be controlled with a single actuating member 420. Alternatively, two or more actuating members can be used to control the one or more restraining mechanisms or members used with stent 430 and filter assembly 450. For instance, one or more restraining mechanisms of members can be used with filter assembly 450, while another one or more restraining mechanisms of members can be used with stent 430. As such, one or more actuating members can be used to control one or more restraining members, in any appropriate combination.

Another exemplary configuration of the present invention is illustrated in FIG. 12. Many of the foregoing aspects of the delivery devices, described herein, apply to delivery device 500 of FIG. 12. For instance, the earlier descriptions of the restraining mechanism also apply to the restraining mechanism of delivery device 500.

As illustrated in FIG. 12, delivery device 500 includes a guide member 512, having a proximal end 516 and a distal end 514. As with the other embodiments of delivery device, a handle 522 cooperates with proximal end 516. This handle 522 receives an actuating member 520 that extends from a restraining mechanism 540, which in turn restrains a stent 530. The actuating member 520 passes from restraining mechanism 540, through an aperture 526 formed in a ferrule 550, and into a lumen 518, which extends to handle 522.

The ferrule 550 mounts on the guide member 512, proximal to the restraining mechanism 540. Ferrule 550 provides a transition between guide member 512 and the structures for supporting a stent 530. With reference to FIG. 13, ferrule 550 has a proximal end 552, a distal end 554, and a lumen 556 extending between proximal end 552 and distal end 554. The aperture 526 communicates with lumen 556 such that actuating member 520 (FIG. 12) can pass through aperture 526 and into lumen 518, and optionally a portion of lumen 556. Ferrule 550 can be fabricated from memory shaped materials, metals, alloys, synthetic materials, natural materials, combinations thereof, and other medical grade materials.

Mounted to distal end 554 of ferrule 550 is an atraumatic tip 560. This tip 560 can have a similar configuration to the other tips described herein. For instance, tip 560 has sufficient flexibility to enable a physician or clinician to steer through a tortuous anatomy of a patient. To aid with this, tip 560 includes a coil 562. Generally, tip 560 can have a variety of other configurations so long as tip 560 is flexible, and/or malleable. Furthermore, tip 560 may be radiopaque to allow steerable positioning of delivery device 500 while allowing a physician or clinician to observe the location of tip 560 using appropriate devices, such as a fluoroscopic device or X-ray device.

Materials that facilitate or provide radiopacity may include, but not limited to, platinum, alloys of platinum, gold, or combinations thereof, metals, alloys, plastic, polymer, synthetic material, combinations thereof, or other materials that provide an appropriate radiopaque signature, while capable of being shaped by a physician or clinician. Alternatively, tip 560 can be a polymer that is mixed, filled, or coated with an appropriate radiopaque material, such as, but not limited to, barium sulphate, bismuth subcarbonate, titanium dioxide, or combinations thereof.

Mounted to tip 560 can be an optional compliant spacer 570. Spacer 570 can be fabricated from a variety of materials. One such material is an elastomeric material. Other materials can include metals, synthetic materials, natural materials, plastics, polymers, or other medical grade materials.

Since the minimum inside diameter of stent 530 can be greater than an outside diameter of tip 560, inclusion of spacer 570 can prevent movement of stent 530 relative to tip 560 as device 500 is steered through the tortuous anatomy of a patient. The spacer 570 can also provide additional structural strength to tip 560 to prevent excessive bending during positioning of device 500. In the event that the inside diameter of stent 530 is the same or substantially the same as the outside diameter of tip 560, spacer 570 may be omitted. This is also true if tip 560 is sufficiently strong to withstanding movement and positioning of device 500 within a patient.

It will be understood that tip 560 can be replaced with, or modified to include, a filter assembly, such as described with device 400. In particular, the filter assembly 450 can be modified to include an elongate body that functions as the portion of tip 560 disposed into ferrule 550, and upon which mounts optional spacer 570 and stent 530. Consequently, delivery device 500 can also include embolic protection.

With continued reference to FIG. 13, ferrule. 550 can optionally include a strut 580. Strut 580 can be added to provide additional structural support to restraining mechanism 540 (FIG. 12), and to aid with removing the restraining mechanism 40 following deployment. For example, as discussed previously, a portion of each restraining mechanism can be attached to guide member 512, and in this particular embodiment, to ferrule 550. When a restraining mechanism is released, a portion of the restraining mechanism may be disposed between the relevant vessel wall and the expanded stent. Thus, strut 580 provides a greater quantity of bonding surface, and/or helps to separate the stent 530 from the vessel wall until the delivery device is removed. In particular, strut 580 provides additional surface area for attaching the sleeve, and aids with creating a gap between the stent 530 and the vessel wall, thus allowing the sleeve to be removed when the delivery device 500 is removed.

Similar to the procedures mentioned above, the delivery device can be removed following performance of a procedure. To achieve this, a capture catheter can be used or more generally a catheter to capture the delivery device. Various catheters are known and can be used to perform this function. Exemplary catheters are described in the U.S. patent applications incorporated herein, but one skilled in the art will appreciate that other catheters can be used.

FIGS. 14A-C illustrates schematic side views of another alternative stent delivery device, similar to those depicted herein, except that the restraining mechanism is released in portions over sequential stages. In particular, an alternative embodiment of a stent delivery device 600 comprises a handle 622 that is operably coupled to an actuating member 620. The actuating member 620, and at least a portion of the handle 622, is disposed within a guide member 612 lumen 618, wherein the guide member 612 comprises a distal end 614 and a proximal end 616.

FIG. 14A further illustrates that a restraining mechanism 640 comprises segmented restraining mechanism sleeves 642a, 642b, and 642c, which are configured to close about a stent 630, when the actuating member 640 is engaged. Each segmented sleeve 642a-c can receive a portion of the actuating member 620 as it is threaded or stitched through to secure the segmented sleeves 642a-c in place. The stitching or threading can be similar to the other configurations described herein.

Thus, as shown in FIG. 14B, the segmented sleeves 642a-c are configured such that the actuating member 620 can be drawn in a proximal direction and disengage only portions of the restraining mechanism sleeves 642a-c at one time. For example, if the actuating member 620 is drawn in the proximal direction a certain distance, only sleeve 642c will become disengaged since the actuating member 20 will be disengaged from the sleeve 642c. At this portion, the stent 630 is therefore allowed to expand as appropriate.

Similarly, if the actuating member 620 is drawn further in the proximal direction, sleeves 642b-c can each become disengaged in a segmented, individual manner. Furthermore, as shown in FIG. 14C, if the actuating member 620 is drawn completely from the restraining mechanism 640, each of sleeves 640a-c will become disengaged, allowing the stent 630 to expand fully along the length of the stent 630. Using segmented sleeves in this manner can aid delivery of the stent 630 to a specific bodily region, particularly when the stent 630 may need to be released in a relatively slow, or only a partial manner.

One will appreciate, therefore, that the present invention may be embodied in other specific forms without departing from its spirit or essential characteristics. For example, the embodiment of FIG. 14A-14C can use any restraining mechanism or member described herein and is not limited to only a "sleeve." Further, each of the foregoing embodiments may be manufactured from a variety of different materials, each within the context of the present invention. In particular, each of the foregoing apparatus described herein can be fabricated from a variety of shaped memory materials, metals, alloys, polymers, plastics, synthetic materials, natural materials, combinations thereof, or other medical grade materials.

Accordingly, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A stent delivery device comprising:
   a guide member having a proximal end and a distal end;
   a stent mounted to said guide member, wherein the stent is spaced proximally from the distal end of the guide member;
   a segmented restraining sleeve disposed about the stent, the restraining sleeve having a first end, a second end, and a plurality of segments, each segment extending from the first end to the second end; and
   an actuating member which cooperates with the first end and second end of the restraining sleeve to maintain said first and second ends in close proximity thereby applying a restraining force to at least a portion of said stent to prevent said stent from expanding, said restraining sleeve cooperatively engaged with the actuating member, so that movement of said actuating member in a proximal direction releases said restraining force to deploy said stent.

2. The device of claim 1, wherein said restraining sleeve is at least partially attached to said guide member.

3. The device of claim 1, wherein said actuating member passes through multiple segments of said sleeve between said first end and said second end in a cooperating fashion.

4. The device of claim 3, wherein movement of said actuating member in a proximal direction releases sequential segments of the sleeve.

5. The device of claim 1, wherein said guide member further comprises a lumen extending from said distal end toward said proximal end.

6. A stent delivery device comprising:
   a guide member having a lumen, a proximal end, and a distal end;
   a stent mounted to said guide member, wherein the stent is spaced proximally from the distal end of the guide member;
   a segmented restraining sleeve disposed about the stent, the restraining sleeve including a first end, a second end, and a plurality of circumferentially-oriented segments; and
   an actuating member disposed within the lumen which cooperates with the first end and second end of the restraining sleeve to maintain said first and second ends in close proximity thereby applying a restraining force to at least a portion of said stent to prevent said stent from expanding, said restraining sleeve cooperating with the actuating member such that movement of said actuating member in a proximal direction releases said restraining force to deploy said stent.

7. The device of claim 6, wherein said lumen cooperates with an aperture in said guide member, said actuating member passing from said guide member to said stent through said aperture and said stent being mounted to said guide member distally of said aperture.

8. The device of claim 6, wherein said restraining sleeve is configured to release only a portion of said stent at a time as said actuating member is moved in a proximal direction.

* * * * *